United States Patent [19]

Welch

[11] 4,368,592

[45] Jan. 18, 1983

[54] SEMI-DWARF MAIZE AND METHOD

[75] Inventor: Vern A. Welch, Fremont, Nebr.

[73] Assignee: DeKalb AgResearch, Inc., DeKalb, Ill.

[21] Appl. No.: 286,858

[22] Filed: Jul. 27, 1981

[51] Int. Cl.³ .............................................. A01H 1/02
[52] U.S. Cl. ................................... 47/58; 47/DIG. 1
[58] Field of Search .............................. 47/58, DIG. 1

[56] References Cited

U.S. PATENT DOCUMENTS 3,710,511  1/1973  Patterson ................................ 47/58

*Primary Examiner*—Robert E. Bagwill
*Attorney, Agent, or Firm*—Kinzer, Plyer, Dorn & McEachran

[57] ABSTRACT

Methods for use of genic dominant semi-dwarfism in the production of commercial hybrid maize including producing and maintaining seed stocks substantially of a homozygous semi-dwarf genotype and stocks substantially of a heterozygous, semi-dwarf allele and a non-semi-dwarf allele, genotype, which provide a semi-dwarf phenotype.

7 Claims, No Drawings

SEMI-DWARF MAIZE AND METHOD

BACKGROUND OF THE INVENTION

This invention relates generally to the production of maize commonly known in the United States as corn and more particularly concerns the development and production of inbred and hybrid semi-dwarf maize with other desired characteristics.

Commercial hybrid maize normally grows to a height of nine to ten feet with each plant having either one or two ears. The ear normally grows about one-third the way up the plant or about three feet from the ground. Consequently the maize plant, while providing a large ear has a substantial leaf and stalk structure and a considerable mechanical stability problem in that the heavy ear is about three feet from the ground with six feet of stalk and the tassels extending above that. In the past, efforts have been made to develop strong branching of secondary roots in maize to help alleviate this problem. While these efforts have improved the mechanical stability of maize considerably, heavy wind storms or rain will still wreak havoc in a field of maize.

Accordingly, one of the objects of this invention is to provide a method to reduce the height of the maize plant thereby improving the mechanical stability of the plant.

While great gains have been made in the use of hybrid maize in the productivity and yield per acre, over that of inbred maize, further substantial gains due to hybrid vigor are not anticipated. Consequently, efforts must be directed to drastically changing the characteristics of the commercial maize plant by genetic or environmental manipulation.

Hence, one of the objects of this invention is to significantly increase the yield per acre of maize. For example, in the Apr. 17, 1974 edition of *The Wall Street Journal*, the article entitled "In Search of Superbean", it was pointed out that soybeans could not easily be hybridized and therefore fell far behind corn in productivity increase. During the period from 1950 to 1973, soybeans increased in productivity from 21.8 to 27.8 bushels per acre while corn increased from 38.4 to 91.4 bushels per acre.

Unfortunately, while hybrid vigor has resulted in great increases in yield it normally causes a similar great increase in height of the maize plant due to the recessive nature of dwarf genes. Thus, to produce recessive dwarf hybrid seeds, care must be taken to shield the plant from possible normal pollen carried from neighboring fields.

SUMMARY OF THE INVENTION

In accordance with the invention, a method of obtaining seed of semi-dwarf maize includes growing a first maize plant including a dominant semi-dwarf height allele, self-pollinating the maize plant, harvesting first generation seed produced on said plant, and growing a second generation of maize plants from the first generation seed, eliminating any normal height maize plants from the second generation before they reach the reproducing stage, self-pollinating the remaining second generation plants which will be of semi-dwarf height, harvesting the second generation seed and isolating seed from each plant as a set, growing a third generation representative sample of plants from each set of isolated second generation seed and pollinating each third generation plant only with pollen from maize plants homozygous for normal height alleles, and collecting seed homozygous for dominant semi-dwarf height alleles from sets of isolated seed of the second generation seed whose third generation representative sample plant exhibit only semi-dwarf height.

DETAILED DESCRIPTION OF THE INVENTION

A cross between two inbred lines, both derived from Hays Golden, produced a semi-dwarf plant rather than the expected normal size hybrid. Seed was collected from this semi-dwarf plant and reproduced to give a semi-dwarf phenotype when crossed with a normal height maize plant. The height gene was isolated and bred into a homozygous line which is available at the U.S. Department of Agriculture, Agricultural Research Service, Western Region, National Seed Storage Laboratory, Colorado State University, Fort Collins, Colo., 80523, as DEKALB Semi-Dwarf Corn Ser. No. 90494, Laboratory No. 2M-2447 no later than the issue date of this patent. Thus it was found that this mutant of maize, not only reproduced but also provided a dominant semi-dwarf phenotype in any maize plant which was crossed with it.

In *Scientific American Plant Life*, 1957 edition, pgs. 221-222, it is stated that there were no dominant dwarf maize plants. Similarly, in *The Mutants of Maize*, published by the Crop Science Society of America, 1968, there are no dominant semi-dwarfs, and at page 55 it shows $D_8$ a dominant dwarf which more resembles a cabbage than a maize plant, however, $D_8$ is undesirable in that the plant is commercially unusable. The present semi-dwarf provides an inbred homozygous for the semi-dwarf allele of about 2 to $3\frac{1}{2}$ feet height and provides a hybrid which is approximately one-third of the normal size of the maize plant.

As herein used, the term semi-dwarf should be interpreted to mean a maize plant on the order of one meter in height, say, within a range of from about 90 to 130 centimeters, with an ear height on the order of about 20 to 40 centimeters.

There are several ways of using this dominant semi-dwarf phenotype. The first is by selfing through a number of generations, say 5 or whatever number is necessary or desirable to fix or achieve homozygosity, whether the source material is homozygous or heterozygous for the semi-dwarf gene. The second is by crossing the original source material of the dominant semi-dwarf gene to one or more known inbreds, which might be termed the elite, and then backcrossing a number of times to the elite line, say through 5 generations which in effect will convert the known inbred to a semi-dwarf type. This amounts to taking the segment of the chromosome that the semi-dwarf is on and transferring it into a normal inbred thereby converting the elite line into a semi-dwarf inbred.

The first, the selfing procedure, has the advantage that it is probably quicker or can be accomplished in a shorter period of time, say something on the order of five years. But the result is a semi-dwarf line that is a totally new inbred line untested in any other sense and may be either superior or inferior to the original semi-dwarf source when used in crosses.

The second, involving outcrossing to one or more known inbred lines followed by backcrossing, has the disadvantage that it will take longer since the same selfing procedure must be employed at the end to fix the homozygosity of the dominant semi-dwarf gene. But it has the advantage that the resultant new inbred will be similar to an established line and at the same time will be semi-dwarf.

Considering the first, i.e. the selfing procedure alone, the source material, i.e. the source plant, may be either homozygous or heterozygous for the semi-dwarf gene, but heterozygous for at least some other genes. Assuming that the source plants are homozygous semi-dwarf, they might be designated DD. This then involves self-pollination of the homozygous semi-dwarf source material, i.e. taking the pollen from the tassel, putting it on the silk, harvesting the seed, and going through this as a cyclical procedure for, say, 5 cycles or whatever number are necessary or considered desirable to achieve general homozygosity. Because the original plant was homozygous for the semi-dwarf, there is no segregation in the subsequent generation and it is considered that after five generations of selfing, the line is virtually homozygous for other characteristics for all intents and purposes. At least at that stage sufficient identity will have been achieved.

The second aspect of selfing is where the source plant is heterozygous for the semi-dwarf gene, which is to say Dd. After selfing, the progeny will be three different types of plants in a ratio of 1 DD, 2 Dd and 1 dd which is the normal genetic segregation ratio. The normal height plants, i.e. the dd types can be eliminated. But the DD and Dd all are semi-dwarf plants and appear the same. Ears from the individual semi-dwarf plants can then be planted out in a progeny row and if the plants from the next generation in a particular row are all semi-dwarf, the parent plant was then DD, i.e. homozygous. But if the plants in a given progeny row are both normal height and semi-dwarf, their parent was Dd, i.e. heterozygous and that row can be either eliminated or handled with the same procedure for additional generations. But as to the homozygous row, the genes are fixed for homozygosity and the selfing procedure referred to previously for homozygous semi-dwarf material, i.e. DD can then be followed. Selecting the homozygous row and following five generations of selfing is the fastest way to achieve homozygosity for new semi-dwarf lines.

Where the semi-dwarf gene is to be used in one or more known inbred lines are outcross and backcross procedure may be used, which is to say that normal inbred lines are converted to a semi-dwarf line for use ultimately in making hybrids. To begin with there is the source of the semi-dwarf gene referred to herein above. There is also the source of a known inbred line which would be from a regular hybrid program. The purpose is to transfer the dwarfing gene from the semi-dwarf source into the normal inbred so that the normal inbred genotype is recovered except for the dwarfing gene, resulting in a semi-dwarf plant leaving everything else the same.

The first step is to cross the dwarf source, designated DD, with the normal inbred, designated dd, which will produce a hybrid, designated $F_1$, which is heterozygous, i.e. Dd. This would be the so-called outcross generation or $F_1$. The $F_1$ seed would then be planted to provide Dd plants which are all semi-dwarf plants. Additional plants from the normal inbred line would then be backcrossed to the Dd plants either by taking Dd pollen to the inbred plant or inbred pollen to the Dd plant. The result is a Dd heterozygous cross to a dd known inbred which will give two types of progeny, the first a Dd and the second a dd. Plants from the dd will be of normal height and can be discarded. The other, i.e. Dd, is the first backcross generation. Seeds from these plants would be planted to produce plants which are backcrossed with plants of the original inbred line in the cyclical process.

This procedure basically is or involves an initial outcrossing of the semi-dwarf source DD to the normal inbred line dd and crossing the semi-dwarf plants back to the normal inbred line, planting the seed, eliminating those of normal height and backcrossing the remaining semi-dwarf to the inbred line for a number of generations, say five or whatever is considered desirable. At that point a Dd version of the known inbred line has been achieved and the approach thereafter to homozygosity of the semi-dwarf gene can be achieved through selfing in the same way as set forth previously.

Semi-dwarf hybrid maize of this type allows for closer spacing per acre due to improved mechanical stability and less leaf area per plant. The dominant nature of the semi-dwarf allows production of hybrids between a semi-dwarf line and an established or commonly available line. The reduced plant and ear height of the dwarf hybrids will permit an increase in the plant population rate per acre with better utilization of the available solar energy. Stalk and root lodging should be reduced because of the reduction in physical stress associated with reduced plant and ear height. The dominant action of the gene causing the semi-dwarf characteristic allows the production of hybrids with either one or both parents of the hybrid carrying the gene in a homozygous condition. The reduction in row width and plant population can result in substantial modification of weed control practices and changes in the type of harvest equipment used.

While the preferred form and several variations of the invention have been shown and described, it should be understood that suitable additional modifications, changes, substitutions and alterations may be made without departing from the invention's fundamental theme.

The embodiments of the invention in which an exclusive property or privilege is claimed are defined as follows:

1. A method of obtaining seeds of dominant semi-dwarf maize, including the steps of:
   growing a first generation maize plant from first generation seed which includes a dominant semi-dwarf height allele;
   self-pollinating the first generation maize plant to produce second generation seed;
   growing a second generation of maize plants from the second generation seed;
   eliminating the normal height maize plants, if any, from the second generation plants;
   self-pollinating the remaining second generation plants to produce third generation seed;
   isolating the third generation seed from each plant as a set from the seed of the remaining second generation plants;
   growing third generation plants on a segregated basis from seed from each set of isolated third generation seed;
   self-pollinating the third generation plants in the isolated sets which are of semi-dwarf height to produce fourth generation seeds;

collecting the fourth generation seed from the sets of isolated seed whose segregated third generation sample plants are all of semi-dwarf height;

and thereafter cyclically growing additional generation of plants from the thus collected fourth generation seed, self-pollinating such plants to produce additional seed from which additional plant generations are grown and self-pollinated to produce additional seed, etc. on a cyclical basis a sufficient number of times to produce final semi-dwarf seed of satisfactory homozygosity.

2. The method of claim 1 further characterized by and including the step of eliminating all of the third generation sources in the isolated sets which have any normal height plants therein.

3. The method of claim 1 further characterized by and including the steps of also self-pollinating the third generation plants of semi-dwarf height in the isolated sets which have both semi-dwarf and normal height plants therein to produce separate fourth generation seeds;

growing separate fourth generation plants from such fourth generation seed;

self-pollinating such fourth generation plants to produce fifth generation seed;

isolating the fifth generation seeds from each plant as a set from the fourth generation plants;

growing fifth generation plants on a segregated basis from a representative sample of seed from each set of isolated fifth generation seed;

collecting the fifth generation seed whose fifth generation sample plants are all of semi-dwarf height;

and thereafter cyclically growing additional generations of plants from the thus collected fifth generation seed, self-pollinating such plants to produce additional seed from which additional plant generations are grown to be self-pollinated to produce additional seed, etc. all on a cyclical basis a sufficient number of times to produce final semi-dwarf seed of satisfactory homozygosity.

4. The method of claim 1 further characterized by and including the step of using seed from the source identified as DEKALB Semi-Dwarf Corn Ser. No. 90494, Laboratory No. 2M-2447, U.S. Department of Agriculture, Agricultural Research Service, Western Region, Colorado State University, Fort Collins, Colo., 80523 as the first generation semi-dwarf seed.

5. The method of claim 1 in which the first generation seed is homozygous as to the dominant semi-dwarf height allele, and no normal height maize plants are produced in the second generation maize plants.

6. A method of converting a normal inbred line of maize plants to a semi-dwarf line including the steps of:

growing a first generation maize plant from first generation seed which includes a dominant semi-dwarf height allele, growing a first generation of maize plants from seed of a normal inbred line;

causing pollination of one such first generation plant with the other to produce second generation seed;

growing a second generation of maize plant from the second generation seed;

crossing the second generation of maize plants with the first generation normal inbred line maize plants to produce third generation seed;

growing third generation maize plants from the third generation seeds;

eliminating the normal height maize plants from the third generation plants;

self-pollinating the remaining third generation plants to produce fourth generation seeds;

isolating the fourth generation seeds from each plant as a set from the remaining third generation plants;

growing fourth generation plants on a segregated basis from seed from each set of isolated fourth generation seed;

self-pollinating the fourth generation plants in the isolated sets which are of semi-dwarf height to produce fifth generation seeds;

collecting the fifth generation seed from the sets of isolated seed whose segregated fourth generation plants are all of semi-dwarf height;

and thereafter cyclically growing additional generation of plants from the thus collected fifth generation seed, self-pollinating such plants to produce additional seed from which additional plant generations are grown and self-pollinated to produce additional seed, etc. on a cyclical basis a sufficient number of times to produce final semi-dwarf seed of satisfactory homozygosity.

7. The method of claim 6 further characterized by and including the step of using seed from the source identified as DEKALB Semi-Dwarf Corn Ser. No. 90494, Laboratory No. 2M-2447, U.S. Department of Agriculture, Agricultural Research Service, Western Region, Colorado State University, Fort Collins, Colo., 80523 as the first generation semi-dwarf seed.

* * * * *